US00PP32759P2

(12) United States Plant Patent
Ruter

(10) Patent No.: US PP32,759 P2
(45) Date of Patent: Jan. 19, 2021

(54) HOLLY PLANT NAMED 'RUTHOL4'

(50) Latin Name: ***Ilex crenata* x *I. maximowicziana***
Varietal Denomination: RutHol4

(71) Applicant: University of Georgia Research Foundation, Inc., Athens, GA (US)

(72) Inventor: John M. Ruter, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 16/602,779

(22) Filed: Dec. 5, 2019

(51) Int. Cl.
*A01H 5/12* (2018.01)
*A01H 6/00* (2018.01)

(52) U.S. Cl.
USPC ..... Plt./247

(58) Field of Classification Search
USPC ..... Plt./247
CPC ..... A01H 5/12; A01H 5/02; A01H 6/00
See application file for complete search history.

*Primary Examiner* — Keith O. Robinson
(74) *Attorney, Agent, or Firm* — Klarquist Sparkman, LLP

(57) ABSTRACT

A new *Ilex* plant named 'RutHol4' is characterized by a combination of an attractive pyramidal growth habit, potential for use in containers or as a small hedge.

2 Drawing Sheets

Genus and species: *Ilex crenata* x *I. maximowicziana.*

Variety denomination: The new *Ilex crenata* x *I. maximowicziana* claimed is of the cultivar denominated 'RutHol4'.

BACKGROUND OF THE INVENTION

The present invention relates to a new and distinct cultivar of a Japanese holly plant named 'RutHol4'. Seed was collected from an unnamed F1 seedling (female) from the original cross of *Ilex crenata* 'Sky Pencil' (unpatented female) x *I. maximowicziana* #10-8S (unpatented male parent) plant.

The new 'RutHol4' variety is a product of a planned breeding program conducted by the inventor (in Watkinsville, Ga.). The objective of the *Ilex* breeding program is to create new plant cultivars with novel forms of growth, good cold hardiness, and resistance to damage from spider mites, insects and diseases.

The new 'RutHol4' plant is thus a product of *Ilex crenata* x *Ilex maximowicziana* F1 seedlings. The cross was made in 2010. The collected seed was sown in fall of 2010 and 276 seedlings were taken to a research nursery in Dearing, Ga. in spring of 2012. 'RutHol4', one of the plants grown from the collected seed, was selected for further evaluation in summer of 2014. 'RutHol4' has been evaluated for container production since 2012.

'RutHol4' has been evaluated through trials at a horticultural farm in Watkinsville, Ga. from 2016.

Asexual reproduction of the new 'RutHol4' variety was by vegetative terminal cuttings in a controlled environment in Dearing, Ga. and Watkinsville, Ga. since 2014. Observations of the new variety have shown that the unique features of this new 'RutHol4' are stable and have reproduced true to type in successive generations.

SUMMARY OF THE INVENTION

The cultivar 'RutHol4' has not been observed under all possible environmental conditions. The phenotype may vary somewhat with variations in environment and cultural practices such as temperature and light intensity without, however, any variance in genotype.

The following represents the distinguishing characteristics of the new *Ilex* cultivar named 'RutHol4'. In combination, these traits set 'RutHol4' apart from all other existing varieties of *Ilex* known to the inventor.

1. 'RutHol4' exhibits an attractive, pyramidal growth habit
2. 'RutHol4' has excellent potential for containers or as a small hedge
3. 'RutHol4' demonstrates a dark new growth
4. 'RutHol4' has a height:width ratio: approx. 1.4:1

BRIEF DESCRIPTION OF THE FIGURES

The accompanying colored photographic illustrations show the overall appearance and distinct characteristics of the new cultivar 'RutHol4'. The colors in the photographs are as close as possible with the photographic and printing technology utilized.

The photograph labeled

The photograph labeled

COMPARISON WITH OTHER VARIETIES

Figure 1:
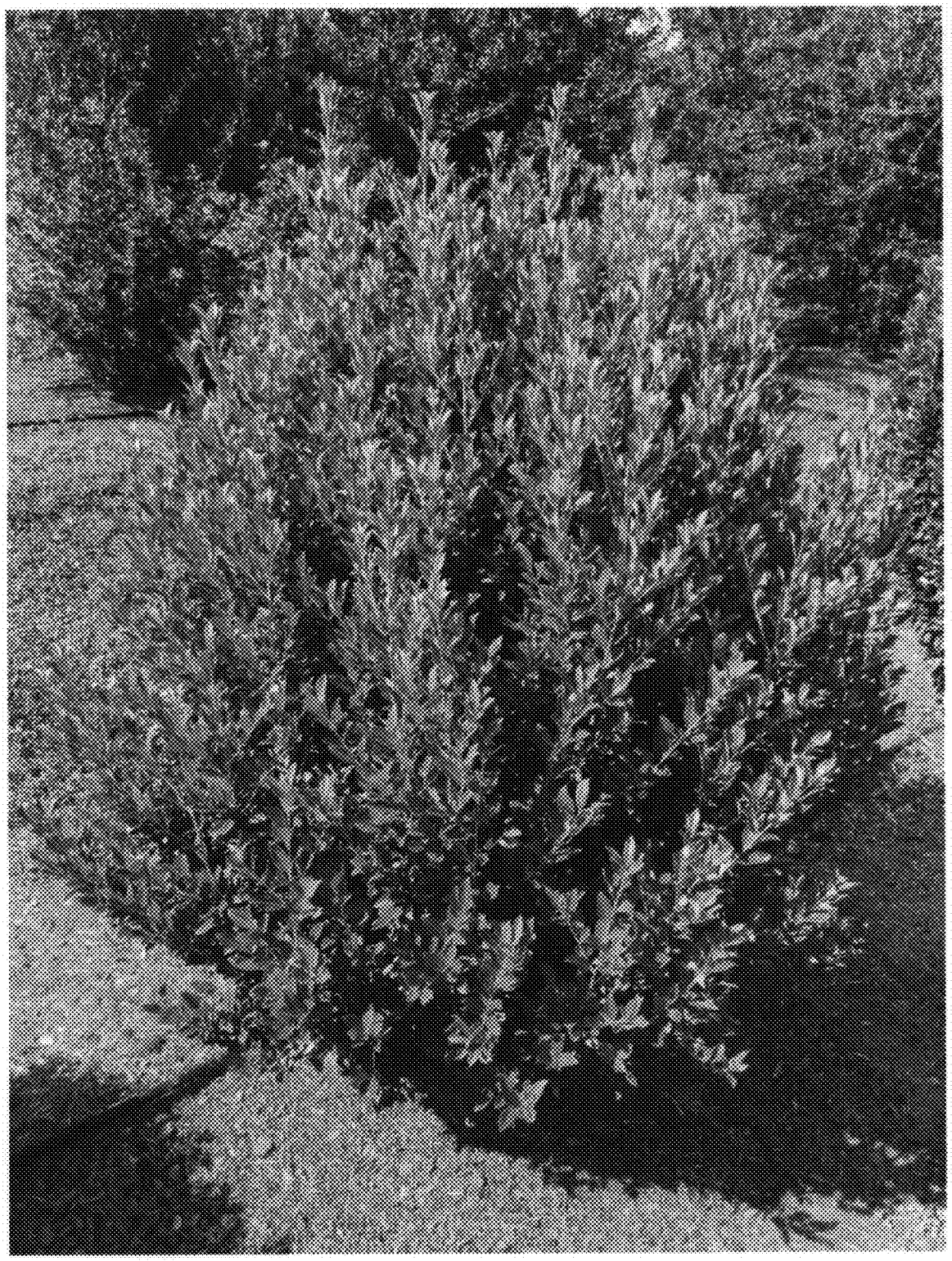
FIG. 1 is a photograph of a three year old (three years from cutting) 'RutHol4' plant depicting the overall plant habit of 'RutHol4'.
Figure 2:
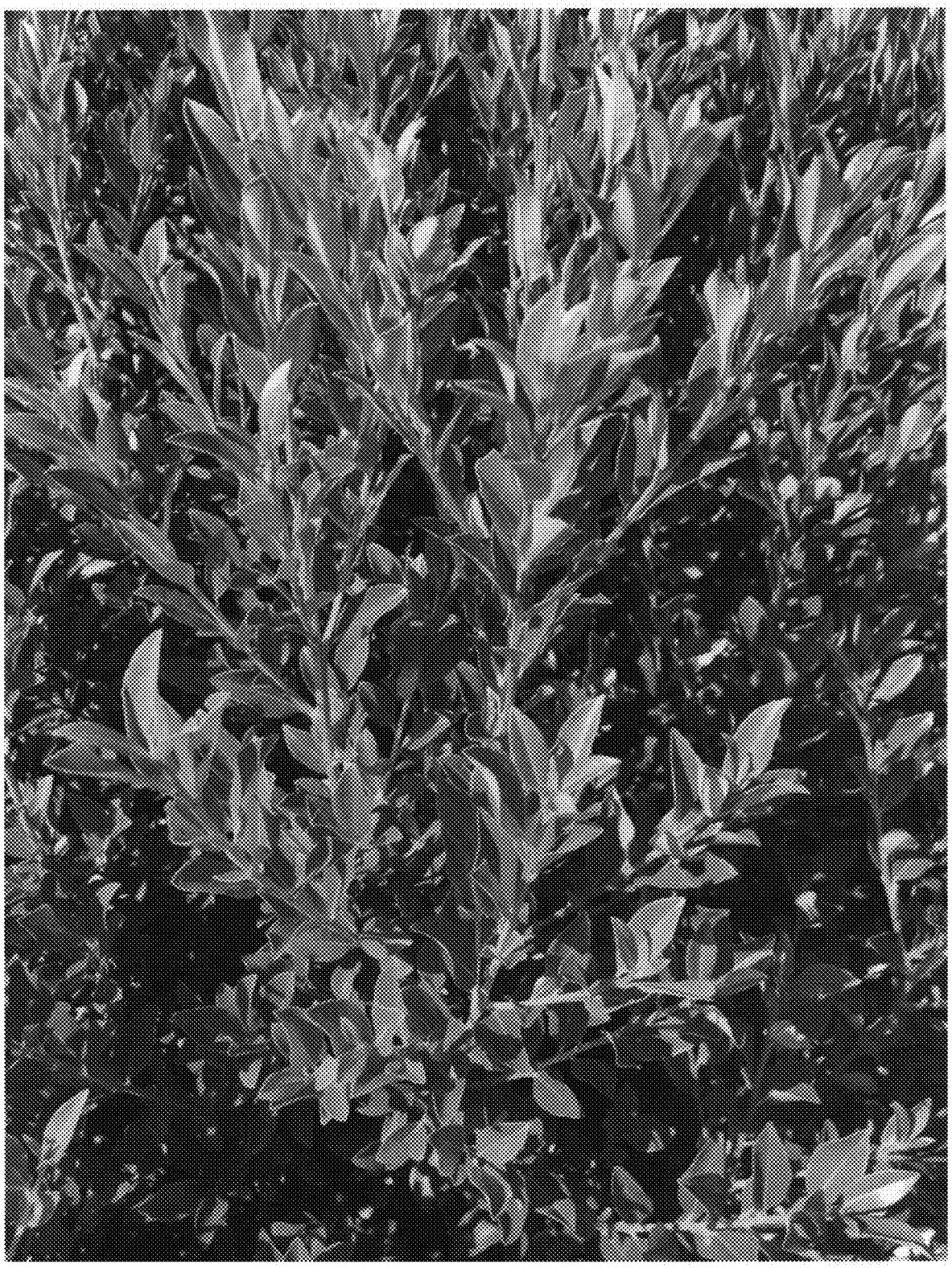
FIG. 2 depicts a close-up view of a portion of the foliage of 'RutHol4' of FIG. 1.

The new 'RutHol4' is a female plant, unlike 'Ruthol1' (U.S. Plant Pat. No. 23,905) which is a male plant. 'RutHol4' is a faster growing plant than 'Sky Pencil'. In one growing trial, four year old (from cutting) 'RutHol4' plants growing in the ground averaged about 172 cm high, while five year old 'Sky Pencil' plants averaged about 117 cm high. The height to width ratio of *Ilex maximowicziana* #10-8S (unpatented) is less than the height to with ratio of 'RutHol4'. In comparison, an eight year old plant of this #10-8S variety had a height to width ratio of 0.6. Also, the leaves of the 'RutHol4' plant are much larger than the leaves of both 'Sky Pencil' and *Ilex maximowicziana* #10-8S. The leaves of the new plant are typically from 3.0 cm to 4.0 cm long in comparison to leaves of these two other plants which are typically 2 cm to 3 cm long.

DETAILED BOTANICAL DESCRIPTION

The following is a detailed description of the *Ilex* cultivar named 'RutHol4'. Data was collected at a horticultural farm in Watkinsville, Ga. from three year old plants grown outdoors and planted in the ground. Throughout this specification, color names beginning with a small letter signify that the name of that color, as used in common speech, is aptly descriptive. Color names beginning with a capital letter designate values based upon The R.H.S. Colour Chart, 6$^{th}$ edition published in 2015 by The Royal Horticultural Society (R.H.S.), London, England.

Parentage:

*Female parent.*—*Ilex crenata* 'Sky Pencil' x *Ilex maximowicziana* (female).

*Male parent.*—*Ilex crenata* 'Sky Pencil' x *Ilex maximowicziana* (male).

Habit: Narrow, densely conical evergreen shrub.

Size of plant: 10-gal. plant 3 years from cutting.

A. *Height.*—190 cm.

B. *Width.*—135 cm.

Stem:

A. *Color.*—Yellow-Green 144A.

B. *Length.*—8-30 cm.

C. *Diameter.*—3 mm.

D. *Texture/pubescence.*—Slightly hispid.

E. *Shape.*—Round.

F. *Odor* (*of bruised stem*).—None.

G. *Internode length.*—0.5-2.5 cm.

H. *Strength.*—Medium.

I. *Branches.*—20-30 main branches with 20-100 lateral branches per main branch.

Leaf:

A. *Type.*—Simple.

B. *Color* (*R.H.S.*).—1. Upper leaf surface: Emerging leaves — Greyed-Orange 165A. Mature leaves — Green 137A. 2. Lower leaf surface: Emerging leaves — Yellow-Green 148A. Mature leaves — Yellow-Green 146B.

C. *Mature size* (*l*×*w*): 3-4 cm×1-1.5 cm.

D. *Apex.*—Acuminate.

E. *Base.*—Cuneate.

F. *Margin.*—Serrulate.

G. *Shape.*—Elliptical.

H. *Lobes* (*present/absent*).—Absent.

I. *Texture/pubescence.*—Smooth, no pubescence (both surfaces).

J. *Arrangement on stem.*—Alternate.

K. *Venation.*—Pinnate.

L. *Texture.*—Leathery.

M. *Aspect.*—45-60°.

N. *Leaves per lateral branch.*—20-50.

O. *Odor when crushed.*—None.

Petiole:

A. *Length.*—5 mm.

B. *Shape.*—Reniform.

C. *Color* (*R.H.S.*).—Yellow-Green 144A.

D. *Texture/pubescence.*—Moderately hispid.

E. *Diameter.*—1 mm.

F. *Strength.*—Weak.

Inflorescence:

A. *Type.*—Solitary in clusters of 1 to 3; female.

B. *Longevity.*—Late April to mid-May in Athens, Ga.

C. *Number per plant.*—10,000-20,000.

Flower:

A. *Number per inflorescence.*—1 — female.

B. *Axillary or terminal.*—Axillary.

C. *Symmetry.*—Regular.

D. *Height and diameter* (*l*×*w*).—3 mm×4 mm.

E. *Fragrance.*—None.

F. *Bud.*—1. Size (L×W): 3 mm×2 mm. 2. Shape: Oval. 3. Color (R.H.S.): Yellow-Green 145C. 4. Texture/Pubescence: Smooth, no pubescence.

G. *Blooms.*—Longevity 3-5 days.

H. *Petals.*—1. Number: 4. 2. Size (L×W): 3 mm×2 mm. 3. Shape: Oval. 4. Apex: Round. 5. Base: Truncate. 6. Margin: Smooth, entire. 7. Color at Peak of Bloom (R.H.S.): Green-White 157A with Green-White 157D along margins and at base. 8. Texture/Pubescence: Smooth, no pubescence. 9. Arrangement: Symmetrical.

I. *Pedicels.*—1. Color (R.H.S.): Yellow-Green 144A. 2. Texture/Pubescence: Mostly smooth with an occasional hair. 3. Length: 4 mm. 4. Aspect: Erect. 5. Strength: Weak.

J. *Sepals.*—1. Number: 4. 2. Size (L×W): 1 mm×2 mm. 3. Shape: Cuspidate. 4. Texture/Pubescence: Smooth, no hairs. 5. Color (R.H.S.): Yellow Green 144A. 6. Apex: Round. 7. Base: Truncate. 8. Margin: Sinuate.

K. *Pistils.*—1. Number: 1. 2. Stigma: a) Shape: Hastate. b) Color (R.H.S.): Yellow 4C with White 155A along margins. c) Texture/Pubescence: Smooth, no pubescence. 3. Style: a) Size (L×W): 1 mm×0.5 mm. b) Color (R.H.S.): White 155A. c) Texture/Pubescence: Smooth, no pubescence. 4. Ovary: a) Size (L×W): 2 mm×2 mm. b) Color (R.H.S.): Yellow-Green 144A. c) Texture/Pubescence: Smooth, no pubescence. d) Position: Hypogynous.

Fruits: None observed.

Seeds: None observed.

Pest and disease resistance: Resistant to spider mites (*Tetranychus urticae*).

Hardiness: Not fully determined. The plants have been grown in USDA zone 8a. Parental species have survived −5° F. with no damage in Blairsville, Ga.

What is claimed is:

1. A new and distinct cultivar of the *Ilex* plant named 'RutHol4' as illustrated and described herein.

* * * * *